United States Patent [19]

Hemmerle et al.

[11] Patent Number: 5,567,725
[45] Date of Patent: Oct. 22, 1996

[54] SUBSTITUTED CYCLOHEXANOL ESTERS, THEIR USE FOR TREATING DISEASES, AND PHARMACEUTICAL PREPARATIONS

[75] Inventors: Horst Hemmerle, Lorsch; Gerrit Schubert, Kelkheim; Peter Below, Frankfurt; Andreas Herling, Bad Camberg; Hans-Jorg Burger, Frankfurt, all of Germany

[73] Assignee: Hoechst Aktiengesellschaft, Frankfurt am Main, Germany

[21] Appl. No.: 388,511

[22] Filed: Feb. 14, 1995

[30] Foreign Application Priority Data

Feb. 16, 1994 [DE]  Germany .................. 44 04 848.3

[51] Int. Cl.$^6$ ................ A61K 31/505; A61K 31/415; C07D 401/12; C07D 401/08; C07D 235/12
[52] U.S. Cl. ............... 514/381; 548/253; 548/310.1; 548/301.4; 548/305.4; 548/306.1; 548/306.4; 548/306.7; 548/307.4; 548/132; 548/307.7; 548/309.7; 548/266.4; 548/263.2; 548/236; 548/204; 548/137; 548/138; 548/129; 548/125; 544/239; 544/370; 514/389; 514/394; 514/383; 514/359; 514/392; 514/390; 514/269; 546/268.7; 546/165; 546/256; 546/268.4; 546/269.1; 546/272.4; 546/271.4; 546/274.4; 546/274.1; 546/275.1; 546/272.7; 546/278.7; 546/282.1; 546/280.4; 546/281.4; 546/15; 546/261; 546/293; 546/273.4; 546/269.7
[58] Field of Search ................. 548/253, 310.1, 548/301.4, 305.4, 306.1, 306.4, 306.7, 307.4, 307.7, 309.7, 266.4, 263.2; 514/389, 381, 394; 544/239

[56] References Cited

U.S. PATENT DOCUMENTS

5,463,062   10/1995   Hemmerle et al. .................. 546/168

FOREIGN PATENT DOCUMENTS

0587087   3/1994   European Pat. Off. ...... A61K 31/215
0587088   3/1994   European Pat. Off. ...... C07C 69/757

OTHER PUBLICATIONS

James Ashmmore, et al., "The Role of Hepatic Glucose–6–phosphatase in the Regulation of Carbohydrate Metabolism", vol. XVII, 92–132 (1959).

Ann Burchell et al., "The Molecular Basis of the Hepatic Microsomal Glucose-6 –phosphatase System", Biochem. Biophys. Acta 1092, 129–137 (1990).

James F. Soodsma et al., "The inhibition by Phlorizin of Kidney Microsomal Inorganic Pyrophosphate–Glucose Phosphotranferase and Glucose –Phosphatase", J. Biol. Chem. 242, 1955–1960 (1967).

Bruce K. Wallin et al., "The Requirement For Membrane Integrity In The Inhibition Of Hepatic Glucose 6–Phosphatase By Sulfhydryl Reagnets And Taurocholate", Biochem. Biophys. Res. Commun. 48, 694–699 (1972).

Michael A. Zoccoli et al., "Effect of Two Inhibitors Of Anion Transport On The Hydrolysis Of Glucose 6–Phosphate By Rat Liver Microsomes", J. Biol. Chem. 255, 1113–1119 (1980).

Wesley K. Canfield et al., "The Glucose–6–phosphatase System In Rat Hepatic Microsomes Displays Hyperbolic Kinetics at Physiological Glucose 6–phosphate Concentrations", J. Biol. Chem. 263, 7458–7460 (1988).

William J. Arion, "Measurement Of Intactness Of Rat Liver Endoplasmic Reticulum ", Methods Enzymol., 174, Academic Press (1989), S.58–67.

J. C. Barriere et al., "Synthesis Of Enantiomerically Pure Substituted Cyclopentenes From (–)–Quinic Acid", Helv. Chim. Acta 66, 269 (1983).

Primary Examiner—Johann Richter
Assistant Examiner—Laura R. Cross
Attorney, Agent, or Firm—Finnegan, Henderson, Farabow, Garrett & Dunner, L.L.P.

[57] ABSTRACT

Cyclohexanol esters of the formula I

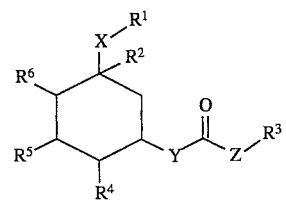

are described in which the radicals have the given meaning.

The compounds are pharmacologically active and may therefore be used as pharmaceuticals, in particular for treating diabetes and other diseases which are characterized by an elevated secretion of glucose from the liver or by an elevated activity of the glucose-6-phosphatase system.

11 Claims, No Drawings

SUBSTITUTED CYCLOHEXANOL ESTERS, THEIR USE FOR TREATING DISEASES, AND PHARMACEUTICAL PREPARATIONS

The disease picture of diabetes is characterized by elevated blood sugar values. In the case of insulin-dependent or type I diabetes, the cause is the death of the insulin-producing β cells of the pancreas; this condition is therefore treated by administering insulin (substitution therapy). By contrast, non-insulin-dependent or type II diabetes is characterized by insulin having a diminished effect on muscle tissue and fat tissue (insulin resistance) and by an increased production of glucose in the liver. The causes of these metabolic disturbances are to a large extent still unclear. While the established therapy using sulfonylureas attempts to compensate for the insulin resistance by increasing the endogenous liberation of insulin, this does not in all cases lead to normalization of the blood sugar level and is not able to halt the progress of the disease; many type II diabetics eventually become insulin-dependent as a result of the β cells becoming "exhausted", and suffer from late damage such as cataracts, nephropathies and angiopathies.

For this reason, novel therapeutic principles for treating type II diabetes are desirable.

In the fasting state, the concentration of glucose in the blood is determined by the glucose production of the liver. A variety of research groups have been able to demonstrate that the increase in the blood sugar values in type II diabetes is correlated with a proportionally elevated output of glucose from the liver. The glucose which is secreted by the liver into the blood can be formed both by degrading liver glycogen (glycogenolysis) and by gluconeogenesis.

Glucose-6-phosphate is the common end product of both gluconeogenesis and glycogenolysis. The terminal step in the hepatic liberation of glucose from glucose-6-phosphate is catalyzed by glucose-6-phosphatase (EC 3.1.3.9). Glucose-6-phosphatase represents a multienzyme complex present in the endoplasmic reticulum (ER). This enzyme complex comprises a glucose-6-phosphate translocase which is present in the ER membrane, a glucose-6-phosphatase which is located on the luminal side of the endoplasmic reticulum and a phosphate translocase [for a review, see: Ashmore J. and Weber G., "The Role of Hepatic Glucose-6-phosphatase in the Regulation of Carbohydrate Metabolism", in Vitamins and Hormones, Vol XVII (Harris R. S., Marrian G. F., Thimann K. V., Edts.), 92 to 132, (1959); Burchell A., Waddell I. D., "The molecular basis of the hepatic microsomal glucose-6-phosphatase system", Bio-chim. Biophys. Acta 1092, 129 to 137, (1990)]. The extensive literature which is available shows that the activity of this multienzyme complex is also elevated under all investigated conditions which, in animal experiments, lead to elevated blood sugar values, e.g. streptozotocin, alloxan, cortisone, thyroid hormones and starvation. In addition to this, a large number of investigations indicate that the elevated production of glucose observed in type II diabetics is associated with elevated glucose-6-phosphatase activity. The importance of the glucose-6-phosphatase system for normal glucose homeostasis is also underscored by the hypoglycemic symptoms of patients suffering from glycogen storage disease type Ib, who lack the translocase component of the glucose-6-phosphate system.

The use of suitable active compounds (inhibitors) to diminish glucose-6-phosphatase activity should result in a decreased liberation of glucose from the liver. These active compounds should be able to adapt the production of glucose by the liver to the actual peripheral consumption. In addition to this, the lower blood glucose values thereby produced in type II diabetics in the fasting state ought also to exert a preventive effect with regard to late damage in diabetes.

A series of non-specific inhibitors of glucose-6-phosphatase has been described in the literature, e.g. phlorrhizin [Soodsma, J. F., Legler, B. and Nordlie, R. C., J. Biol. Chem. 242, 1955 to 1960, (1967)], 5,5'-dithiobis-2-nitrobenzoic acid [Wallin, B. K. and Arion, W. J., Biochem. Biophys. Res. Commun. 48, 694 to 699, (1972)], 2,2'-diisothiocyanatostilbene and 2-isothiocyanato-2'-acetoxystilbene [Zoccoli, M. A. and Karnowski, M. L., J. Biol. Chem. 255, 1113 to 1119, (1980)]. The first therapeutically utilizable inhibitors of the glucose-6-phosphatase system are proposed in European Patent Applications No. 93 114 260.8 and No. 93 114 261.6.

The cyclohexane derivatives which are characterized in detail below are novel compounds which have not previously been described in the chemical and biological literature. We have now found that esters of certain cyclohexanol derivatives, e.g. the compound according to Example 4, are very good inhibitors of the glucose-6-phosphatase system.

The invention therefore relates to cyclohexanol esters of the formula I

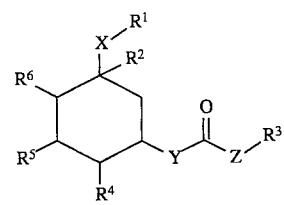

in which the radicals have the following meaning:

$R^1$ is $CONHCOR^{15}$, $CSNHR^{15}$, $CONHSO_2R^{14}$, $CSNHSO_2R^{14}$ or $CH_2NHSO_2R^{14}$, or $R^1$ is a radical selected from the following formulae:

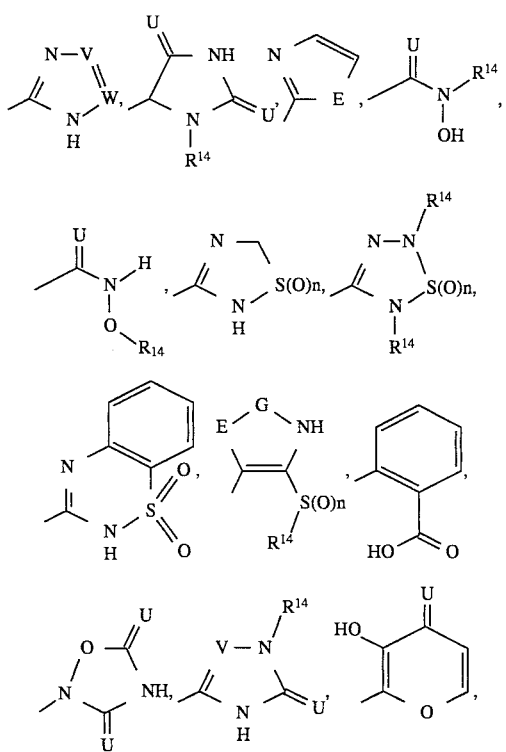

-continued

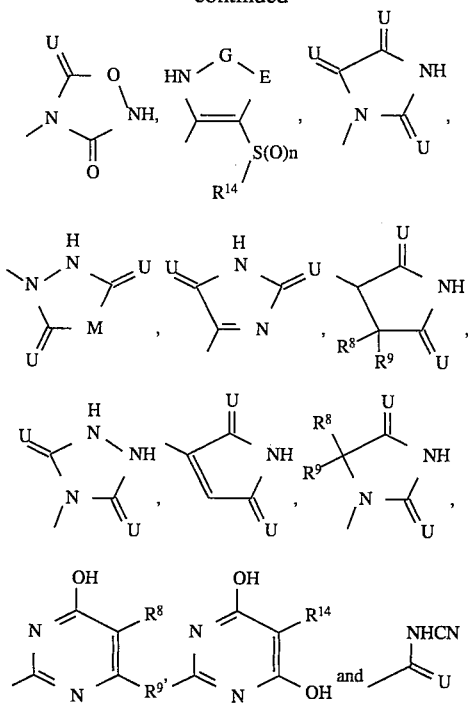

in which V is N or CH, W is N or CH, U is O or S, E is $NR^{14}$, O, S or NH, G is —N=, —O—, —S— or

M is $NR^{14}$, NH, $CH_2$ or $CR^8R^9$, and aromatic rings can be substituted once or more than once by F, Cl, Br, I, OH, O—$C_1$-$C_4$-alkyl, $C_1$-$C_4$-alkyl, $CF_3$, $NO_2$ or CN, or $R^1$ forms, together with $R^2$, the ring

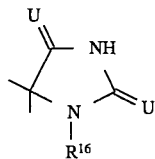

$R^2$ is $C_1$-$C_{10}$-alkyl ($R^{11}$) n, O—$C_1$-$C_{10}$-alkyl($R^{11}$)n, $C_2$-$C_{10}$-alkenyl($R^{11}$)n, O—$C_3$-$C_{10}$-alkenyl($R^{11}$)n, $C_2$-$C_{10}$-$C_{10}$-alkynyl($R^{11}$)n, O—$C_3$-$C_{10}$-alkynyl($R^{11}$)n, S—$C_1$-$C_{10}$-alkyl ($R^{11}$)n, S—$C_3$-$C_{10}$-alkenyl($R^{11}$)n, S—$C_3$-$C_{10}$-alkynyl($R^{11}$)n, NH—$C_1$-$C_{10}$-alkyl($R^{11}$)n, NH—$C_3$-$C_{10}$-alkenyl($R^{11}$)n or NH—$C_3$-$C_{10}$-alkynyl($R^{11}$)n, where $R^{11}$ is optionally substituted by $R^{12}$;

$R^3$, $R^{11}$ and $R^{13}$ are alkyl having from 1 to 10 carbon atoms, cycloalkyl having from 3 to 8 ring carbon atoms, phenyl, naphthyl, phenanthryl, pyridyl, thienyl, furyl, pyrimidyl, indolyl, imidazolyl, coumarinyl, phthaliminyl, quinolyl, piperazinyl, tetrazolyl, triazolyl, oxazolyl or their thieno-fused, pyridino-fused, pyrimidino-fused or benzo-fused derivatives, where the aromatic radical or heteroaromatic radical can be substituted once or more than once, identically or differently, by F, Cl, Br, I, OH, —$NO_2$, CN, $C_1$-$C_4$-alkoxy, $C_1$-$C_4$-alkyl, $NR^8R^9$, phenyl, benzyl, thienyl, furyl, imidazolyl, pyridyl, O-phenyl or O-benzyl, and $R^3$, $R^{11}$ and $R^{13}$ are identical or different;

$R^4$, $R^5$ and $R^6$ are H, OH, an OH group protected by customary alcohol protective groups, F, Cl or Br, or have the meanings given for $R^2$, where $R^4$, $R^5$ and $R^6$ are identical or different;

$R^7$ is $C_1$-$C_4$-alkyl, phenyl or benzyl; $R^8$ and $R^9$ are H, $C_1$-$C_4$-alkyl, $C_1$-$C_4$-alkanoyl or phenyl which is optionally substituted by F, Cl, Br, I, OH, O—$C_1$-$C_4$-alkyl, $CF_3$, —$NO_2$ or CN, where $R^8$ and $R^9$ are identical or different, or $R^8$ and $R^9$ form, together with the nitrogen atom, a 4- to 10-membered, saturated heterocyclic ring in which a $CH_2$ group can be optionally replaced by O, S or $NR^{10}$, $R^{10}$ is H, $C_1$-$C_4$-alkyl, phenyl or benzyl;

$R^{12}$ is phenyl, naphthyl, phenanthryl, pyridyl, thienyl, furyl, thiazolyl, pyrimidyl, indolyl, imidazolyl, coumarinyl, phthaliminyl, quinolyl, piperazinyl, tetrazolyl, triazolyl, oxazolyl or their thieno-fused or benzo-fused derivatives, where the aromatic radical or heteroaromatic radical can be substituted once or more than once, identically or differently, by F, Cl, Br, I, OH, $CF_3$, —$NO_2$, CN, $C_1$-$C_4$-alkoxy, $C_1$-$C_4$-alkyl, $NR^8R^9$, phenyl, benzyl, thienyl, furyl, imidazolyl, pyridyl, O-phenyl or O-benzyl;

$R^{14}$ is hydrogen, $C_1$-$C_{10}$-alkyl, phenyl, naphthyl, phenanthryl, pyridyl, thienyl, furyl, thiazolyl, pyrimidyl, indolyl, imidazolyl, coumarinyl, phthaliminyl, quinolyl, piperazinyl, tetrazolyl, triazolyl, oxazolyl or their thieno-fused or benzo-fused derivatives, where the aromatic radical or heteroaromatic radical can be substituted once or more than once, identically or differently, by F, Cl, Br, I, OH, $CF_3$, —$NO_2$, CN, $C_1$-$C_4$-alkoxy, $C_1$-$C_4$-alkyl, $NR^8R^9$, phenyl, benzyl, thienyl, furyl, imidazolyl, pyridyl, O-phenyl or O-benzyl, or $R^{14}$ is a radical of the formula

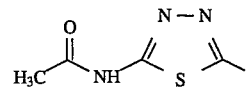

$R^{15}$ is $C_3$-$C_{10}$-alkenoyl, $C_3$-$C_{10}$-alkenoyl($R^{12}$), $C_1$-$C_{10}$-alkanoyl($R^{12}$), phenyl, naphthyl, phenanthryl, pyridyl, thienyl, furyl, thiazolyl, pyrimidyl, indolyl, imidazolyl, coumarinyl, phthaliminyl, quinolyl, piperazinyl, tetrazolyl, triazolyl, oxazolyl or their thieno-fused or benzofused derivatives, where the aromatic radical or heteroaromatic radical can be substituted once or more than once, identically or differently, by F, Cl, Br, I, OH, $CF_3$, —$NO_2$, CN, $C_1$-$C_4$-alkoxy, $C_1$-$C_4$-alkyl, $NR^8R^9$, phenyl, benzyl, thienyl, furyl, imidazolyl, pyridyl, O-phenyl or O-benzyl;

$R^{16}$ is $C_1$-$C_{10}$-alkyl ($R^{11}$)n, $C_3$-$C_{10}$ alkenyl($R^{11}$)n or $C_3$-$C_{10}$-alkynyl($R^{11}$)n, where $R^{11}$ is optionally substituted by $R^{12}$, X is $(CH_2)m$, —CH=CH—, —C≡C—, —$CH_2$—O—$CH_2$—, —$CH_2$—S—$CH_2$— or

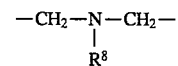

Y is $(CH_2)_m$, O, S or $NR^8$,

Z is $(CH_2)_m$, S, O, S—$C_1$-$C_{10}$-alkyl, O—$C_1$-$C_{10}$-alkyl, CH=CH, CH=CF, CH=CCl, CH=CBr, $CH_2$—CO, $CH_2$—CHF, $CH_2$—CHCl, $CH_2$—CHBr, $CH_2$—CHI, $C_3$-$C_{10}$-cycloalkylene, $C_3$-$C_{10}$- cycloalkenylene, where from 1 to 3 ring carbon atoms can be replaced by sulfur atoms, oxygen atoms or nitrogen atoms, $COOR^7$, C≡C, CH=C (C$_1$-C$_4$-alkyl), CH=C (CN), CH=C (NR$^8$R$^9$), CH=C (C$_1$-C$_4$-alkanoyl), CH=C (R$^{13}$) or NR$^8$, and, if Y is oxygen,

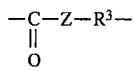

can together be an amino acid residue, selected from the group consisting of Ala, Arg, Asn, Asp, Cys, Gln, Glu, Gly, His, Ile, Leu, Lye, Phe, Pro, Ser, Thr, Trp, Tyr and their derivatives protected by customary protective groups, n is zero, 1 or 2, m is zero, 1, 2, 3 or 4.

Insofar as they contain a carboxyl group, the novel compounds of the formula I can form salts with inorganic or organic bases. The invention also relates, therefore, to the physiologically tolerated salts of compounds of the formula I. The novel compounds of the formula I contain a number of stereocenters. The invention relates to all possible enantiomers and diastereomers. They are all represented by the formula I.

Unless otherwise indicated, the following applies to the statements made above and below:

The alkyl, alkanolyl and alkoxy radicals given under R$^1$, R$^3$, R$^7$, R$^8$, R$^9$, R$^{10}$, R$^{11}$, R$^{12}$, R$^{13}$, R$^{15}$, R$^{16}$ and Z are straight-chain or branched.

The alkyl, alkenyl and alkynyl groups given under R$^2$ and R$^{14}$ are straight-chain, branched or cyclic, it also being possible for only a part of the radical to form a ring. In addition, one of the CH$_2$ groups can be replaced by O, S, SO, SO$_2$ or NR$^8$, R$^{11}$ can be substituted by R$^{12}$, and, when n is 2, the two radicals R$^{11}$ are identical or different.

Unsaturated radicals are unsaturated once or more than once.

Alcohol protective groups are:

Substituted ethers, such as methoxymethyl, methylthiomethyl, t-butylthiomethyl, benzyloxymethyl, p-methoxybenzyloxymethyl, t-butoxymethyl, siloxymethyl, 2-methoxyethoxymethyl, 1-ethoxyethyl, allyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl and 4-picolyl.

Protective groups for the amino acid are:

a) Carbamates, such as methyl and ethyl, 9-fluorenylmethyl; 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, 4-methoxyphenacyl, 2,2,2-trichloroethyl, 2-trimethylsilylethyl, 2-phenylethyl, 1-(1-adamantyl)-1-methylethyl, 1-dimethyl-2-haloethyl, 1,1-dimethyl-2,2-dibromoethyl, 1,1-dimethyl-2,2,2-trichloroethyl, 1-methyl-1-(4-biphenyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkylthio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl, t-amyl, S-benzylthiocarbamate, p-cyanobenzyl, cyclobutyl, cyclohexyl, cyclopentyl, cyclopropylmethyl, p-decyclobenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di-(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium) benzyl and 2,4,6-trimethylbenzyl.

b) Urea derivatives, such as phenothiazinyl-(10)-carbonyl derivatives, N'-p-toluenesulfonylaminocarbonyl and N'-phenylaminothiocarbonyl.

c) Amides, such as N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivatives, N-benzoyl and N-p-phenylbenzoyl.

Compounds of the formula I are preferred in which

R$^1$ is CONHCOR$^{15}$, CSNHR$^{15}$, CONHSO$_2$R$^{14}$, CSNHSO$_2$R$^{14}$ or CH$_2$NHSO$_2$R$^{14}$, or is a radical of the following formulae:

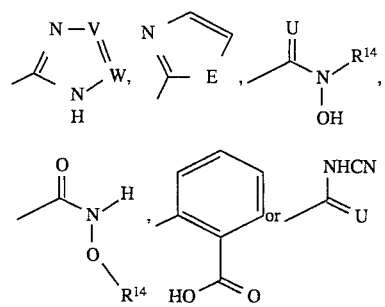

in which E is O, S or NH, R$^{14}$ is H, U is O or S, V is N or CH, W is N or CH, and aromatic rings can be substituted once or more than once by F, Cl, Br, I, OH, O—C$_1$-C$_4$-alkyl, C$_1$-C$_4$-alkyl, CF$_3$, NO$_2$ or CN, or R$^1$ forms, together with R$^2$, the ring

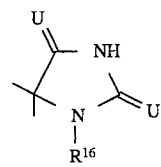

R$^2$ has the following meanings: O—C$_1$-C$_{10}$-alkyl (R$^{11}$)$_n$, (n is 0, 1 or 2), where the alkyl moiety is unbranched, branched or cyclic, and R$^{11}$ can be substituted by R$^{12}$, and, when n is 2, the two radicals R$^{11}$ are identical or different, O—C$_3$-C$_{10}$-alkenyl(R$^{11}$)$_n$, (n is 0, 1 or 2), where the alkenyl moiety is unbranched, branched or cyclic, and is unsaturated once or more than once, and R$^{11}$ can be substituted by R$^{12}$, O—C$_3$-C$_{10}$-alkynyl(R$^{11}$)$_n$, (n is 0, 1 or 2), where the alkynyl moiety is unbranched, branched or cyclic, and is unsaturated once or more than once, and R$^{11}$ can be substituted by R$^{12}$, R$^3$ to R$^{15}$ have the meanings given above, and X, Y, Z and R$^{16}$ have the following meanings:

X is (CH$_2$)$_m$, (m is 0, 1, 2, 3 or 4), CH=CH, C≡C, CH$_2$OCH$_2$ or CH$_2$SCH$_2$,

Y is (CH$_2$)$_m$, (m is 0, 1, 2, 3 or 4), O, S or NR$^8$,

Z is (CH$_2$)$_m$, (m is 0, 1, 2, 3 or 4), S, O, S—C$_1$-C$_{10}$-alkyl, CH=CH, CH=CF, CH=CCl, CH=CBr, CH$_2$—C(O), CH$_2$—CHF, CH$_2$—CHCl, CH$_2$—CHBr, CH$_2$—CHI, C$_3$-C$_{10}$-cycloalkylene, C$_3$-C$_{10}$-cycloalkenylene, COOR$^7$, C≡C, CH=C(C$_1$-C$_4$-alkyl), CH=C(CN), CH=C(R$^{13}$) or NR$^8$.

$R^{16}$ is $C_1$–$C_{10}$-alkyl$(R^{11})$n, $C_3$–$C_{10}$-alkenyl$(R^{11})$n or $C_3$–$C_{10}$-alkynyl$(R^{11})$n, with n in each case being zero or one.

In formula I, the radicals have, in particular, the following meanings:

$R^1$ is CONHCOR$^{15}$, CSNHR$^{15}$, CONHSO$_2$R$^{14}$, CSNHSO$_2$R$^{14}$ or a radical of the formulae:

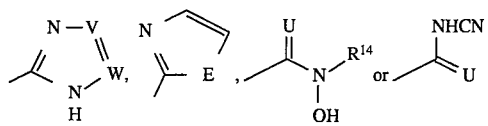

in which E is O, S or NH, $R^{14}$ is H, U is O or S, V is N or CH, W is N or CH, and aromatic rings can be substituted once or more than once by F, Cl, Br, I, OH, O—$C_1$–$C_4$-alkyl, $C_1$–$C_4$-alkyl, CF$_3$, NO$_2$ or CN, or $R^1$ forms, together with $R^2$, the ring

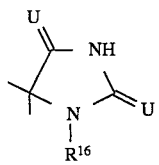

$R^2$ is O—$C_1$–$C_{10}$-alkyl$(R^{11})_n$, (n is 0, 1 or 2), where the alkyl moiety is unbranched, branched or cyclic, and $R^{11}$ can be substituted by $R^{12}$, O—$C_3$–$C_{10}$-alkenyl$(R^{11})_n$, (n is 0, 1 or 2), where the alkenyl moiety is unbranched, branched or cyclic, and is also unsaturated once or more than once, and $R^{11}$ can be substituted by $R^{12}$, O—$C_3$–$C_{10}$-alkynyl$(R^{11})_n$, (n is 0, 1 or 2), where the alkynyl moiety is unbranched, branched or cyclic, is unsaturated once or more than once, and $R^{11}$ can be substituted by $R^{12}$, $R^3$ to $R^{15}$ have the meanings given above, X is (CH$_2$)$_m$, (m is 0, 1, 2, 3 or 4), CH=CH, C≡C, CH$_2$OCH$_2$ or CH$_2$SCH$_2$, Y is (CH$_2$)$_m$, (m is 0, 1, 2, 3 or 4), O, S or NR$^8$, Z is (CH$_2$)$_m$, (m is 0, 1, 2, 3 or 4), S, O, S—$C_1$–$C_{10}$-alkyl, (unbranched or branched), CH=CH, CH=CF, CH=CCl, CH=CBr, CH$_2$—C(O), CH$_2$—CHF, CH$_2$—CHCl, CH$_2$—CHBr, CH$_2$—CHI, $C_3$–$C_{10}$-cycloalkylene, $C_3$–$C_{10}$-cycloalkenylene, COOR$^7$, C≡C, CH=C($C_1$–$C_4$-alkyl) (unbranched or branched), CH=C(CN), CH=C (R$^{13}$) or NR$^8$, $R^{16}$ is $C_1$–$C_{10}$-alkyl$(R^{11})_n$, $C_3$–$C_{10}$-alkenyl$(R^{11})_n$ or $C_3$–$C_{10}$-alkynyl$(R^{11})_n$, with n in each case being zero or 1.

The following meanings of the radicals in formula I are very particularly preferred:

$R^1$ is CONHSO$_2$R$^{14}$ or a radical of the following formulae:

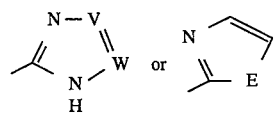

in which E is O, V is N and W is N, or $R^1$ forms, together with $R^2$, the ring

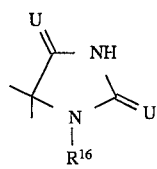

in which U is oxygen, $R^2$ is O—$C_1$–$C_6$-alkyl$(R^{11})$ (n is 1), where the alkyl moiety is unbranched, branched or cyclic, or O—$C_3$–$C_6$-alkenyl$(R^{11})_n$ (n is 1) where the alkenyl moiety is unbranched, branched or cyclic, $R^3$, $R^{11}$ and $R^{13}$ are phenyl, phenyl substituted by OH or chlorine, imidazolyl or benzo-fused or pyridino-fused imidazolyl, where $R^3$, $R^{11}$ and $R^{13}$ are identical or different.

$R^4$, $R^5$ and $R^6$ are H or OH, where $R^4$, $R^5$ and $R^6$ are identical or different.

$R^8$ and $R^9$ are $C_1$–$C_4$-alkyl.

$R^{14}$ is $C_1$–$C_4$-alkyl, phenyl, naphthyl, thiazolyl or its benzo-fused derivatives, where the aromatic radical or heteroaromatic radical can be monosubstituted or disubstituted by chlorine, CF$_3$, NO$_2$, $C_1$–$C_4$-alkoxy or NR$^8$R$^9$, or $R^{14}$ is a radical of the formula

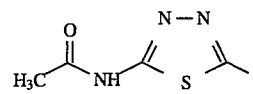

$R^{16}$ is $C_1$–$C_4$-alkyl$(R^{11})_n$, with n being 1.

Insofar as they contain a carboxyl group, the novel compounds of the formula I can form salts with inorganic or organic bases. Salts with inorganic bases are preferred, particularly the physiologically harmless alkali metal salts, especially sodium salts and potassium salts. The compounds of the formula I inhibit the glucose-6-phosphatase system of the liver in mammals. The compounds are therefore suitable for use as pharmaceuticals. The invention also relates, therefore, to pharmaceuticals based on the compounds of the formula I, where appropriate in the form of the physiologically tolerated salts.

The invention furthermore relates to the use of compounds of the formula I, or of the salts, for treating diseases which are associated with an elevated activity of the glucose-6-phosphatase system.

The invention also relates, therefore, to the use of compounds of the formula I, or of the salts, for treating diseases which are associated with an elevated production of glucose from the liver.

The invention also relates to the use of compounds of the formula I, or of the salts, for treating type II diabetes (non-insulin-dependent or maturity-onset diabetes).

The invention furthermore comprises the use of compounds of the formula I, or of the salts, for preparing pharmaceuticals for treating diabetes and other diseases which are characterized by an elevated secretion of glucose from the liver or by an elevated activity of the glucose-6-phosphatase system.

The effect of the novel compounds on the glucose-6-phosphatase system was investigated in an enzyme test using liver microsomes.

Fresh livers from male Wistar rats were used for preparing the microsome fraction containing glucose-6-phosphatase and were processed as described in the literature [Canfield, W. K. and Arion, W. J., J. Biol. Chem. 263, 7458 to 7460, (1988)]. This microsome fraction can be stored at −70° C. for at least 2 months without any significant loss of activity. The glucose-6-phosphatase activity was detected, as described in the literature (Arion, W. J. in Methods Enzymol. 174, Academic Press 1989, pages 58 to 67), by determining the phosphate liberated from glucose-6-phosphate. 0.1 ml of test mixture contained glucose-6-phosphate (1mmol/l), the test substance, 0.1 mg of microsome fraction and 100 mmol/l HEPES buffer (4-(2-hydroxyethyl)piperazine-1-ethanesulfonic acid), pH 7.0. The reaction was started by adding the enzyme. After proceeding at room temperature for 20 minutes, the reaction was stopped by adding 0.2 ml of phosphate reagent. The sample was incubated at 37° C. for 30 minutes and the absorption (A) of the blue color was then measured at 570 nm. The inhibitory activity of the test substance was obtained by comparing with a control reaction which did not contain any test substance, according to the formula $$\text{Percent inhibition} = \frac{A(\text{control}) - A(\text{test substance})}{A(\text{control})} \times 100$$

If necessary, the inhibitory activity of the test substance was determined as a function of the concentration of the test substance employed and, from this, the concentration was calculated which was required to inhibit the enzyme activity by 50% ($IC_{50}$).

The $IC_{50}$ value was determined for the compounds listed below:

| Compound | $IC_{50}$ [μm]: |
|---|---|
| 4 | 0.02 |
| 9 | 0.3 |
| 19 | 0.8 |

The invention also relates to a pharmaceutical which contains one or more novel compounds of the formula I and/or its/their pharmacologically tolerated salts.

The pharmaceuticals are prepared by processes which are known per se and with which the person skilled in the art is familiar. As pharmaceuticals, the novel, pharmacologically active, compounds (= active compound) are either employed as such or, preferably, in combination with suitable pharmaceutical auxiliary substances, in the form of tablets, coated tablets, capsules, suppositories, emulsions, suspensions, granules, powders, solutions or preparations having a protracted release of active compound, with the content of active compound advantageously being from 0.1 to 95%.

Owing to his specialist knowledge, the person skilled in the art is familiar with those auxiliary substances which are suitable for the desired pharmaceutical formulation. In addition to solvents, gel formers, suppository bases, tablet adjuvants and other active compound excipients, antioxidants, dispersants, emulsifiers, defoamers, taste corrigents, preservatives, solubilizers or dyes can, for example, also be used.

The active compounds may be administered topically, orally, parenterally or intravenously, with the preferred mode of administration depending on the disease to be treated. Oral administration is preferred.

For a form for oral use, the active compounds are mixed with the additives which are suitable for this purpose, such as carrier substances, stabilizers or inert diluents, and brought by customary methods into suitable forms for administration, such as tablets, coated tablets, hard gelatin capsules, aqueous, alcoholic or oily suspensions, or aqueous, alcoholic or oily solutions. Examples of inert excipients which can be used are gum arabic, magnesium hydroxide, magnesium carbonate, potassium phosphate, lactose, glucose or starch, in particular corn starch. In this context, the formulation can be effected as a dry granulate or as a wet granulate. Suitable oily carrier substances or solvents are vegetable or animal oils, such as sunflower oil or cod liver oil.

For subcutaneous or intravenous administration, the active compounds, or their physiologically tolerated salts, are brought into solution, suspension or emulsion, if desired together with the substances which are customary for this purpose, such as solubilizers, emulsifiers or other auxiliary substances. Examples of suitable solvents are water, physiological sodium chloride solution or alcohols, e.g. ethanol, propanol or glycerol, and, in addition, also sugar solutions such as glucose solutions or mannitol solutions, or else a mixture of different solvents.

Eyedrops, which contain the active compound in aqueous or oily solution, are suitable pharmaceutical preparations for topical and local use. Aerosols and sprays, and also coarse powders, which are administered through the nostrils by means of rapid inhalation, and especially nose drops, which contain the active compounds in aqueous or oily solution, are suitable for use on the nose.

The dosage of the active compound of the formula I to be administered, and the frequency of administration, depend on the strength and the duration of the effect of the novel compound used; also on the nature and severity of the disease to be treated and on the sex, age, weight and individual responsiveness of the mammalian subject to be treated. On average, the recommended daily dose of a novel compound is, in the case of a mammalian subject—most importantly a human patient—of approximately 75 kg in weight, in the range of from about 1 to 500 mg, preferably from about 10 to 250 mg, it being possible, according to requirement, for the administration to take place in several doses per day, and also, where appropriate, to be lower or higher.

The preparation of the novel compounds of the formula I is elucidated by the examples. Room temperature denotes a temperature of from 20° to 25° C.

EXAMPLE 1

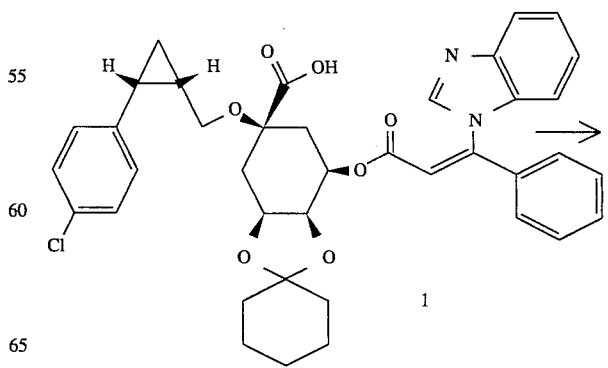

-continued

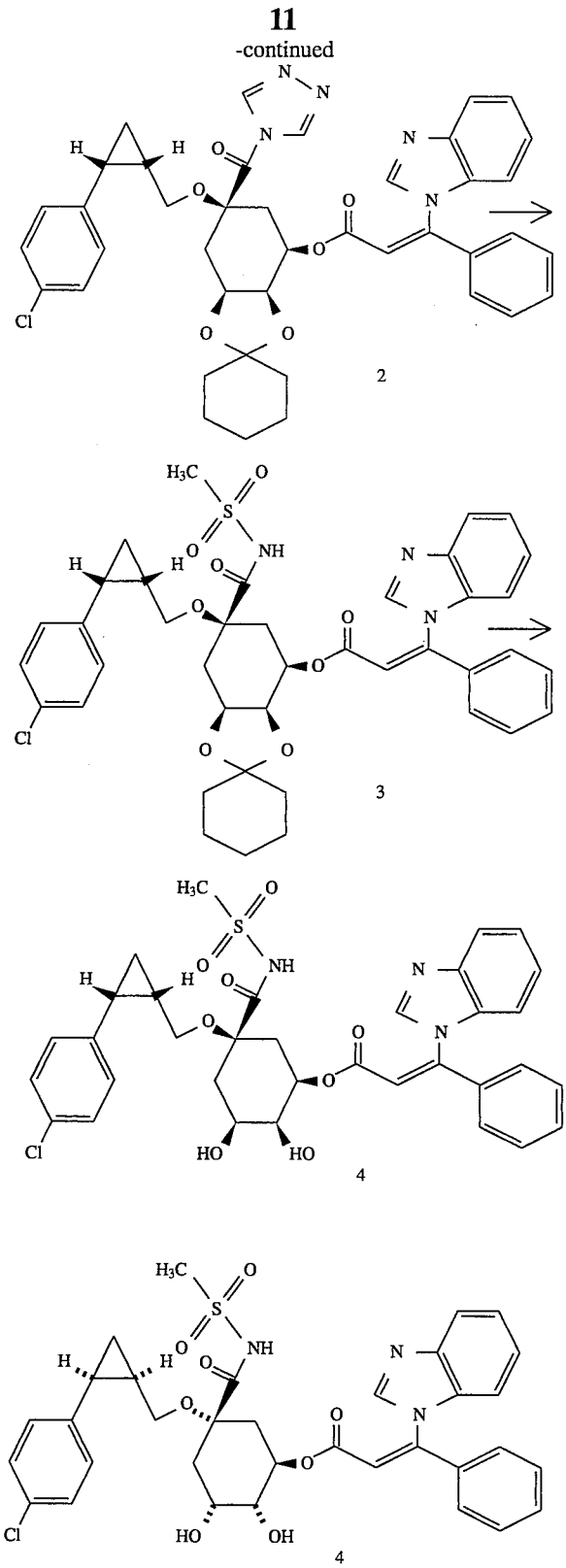

2

3

4

MS(FAB):m/z = 680(M + H⁺)

Preparation of compound 2 from 1

3.7 g (0.054 mol) of the carboxylic acid 1 (preparation cf. EP Application No. 93 114 261.6, reaction scheme method A, structural element 68B) were dissolved in 36 ml of anhydrous dimethylformamide, and 1.81 g (0.011 mol) of N,N'-carbonyldi-(1,2,4-triazole) were added, at room temperature and under argon, to this solution, which was then heated at from 50° to 60° C. for 1.5 hours. After it had been cooled down, the 0.15 molar solution of 2 was employed in the subsequent step without any further working-up.

Preparation of compound 3 from 2

0.057 g (0.006 mol) of methanesulfonamide was dissolved in 3 ml of anhydrous dimethylformamide, and 0.02 g (0.0066 mol) of sodium hydride (80% in oil) was added at room temperature. The suspension was stirred at from 50° to 60° C. for 45 minutes. 3.1 ml (0.00047 mol) of the 0.15 molar triazolide solution 2 were then added dropwise at this temperature. The reaction mixture was stirred at 60° C. for 1 hour. It was then added to a saturated solution of ammonium chloride, whereupon the product 3 precipitated out as an amorphous solid. The precipitate was filtered off with suction and then washed with distilled water; the solid thus obtained was then dried over calcium chloride at $10^{-2}$ Torr and 40° C. for 3 hours. 0.248 g of compound 3 was obtained.

Preparation of compound 4 from 3

0.24 g (0.000316 mol) of cyclohexylidene ketal 3 was initially introduced in 10 ml of dioxane, and 1.6 ml (0.0032 mol) of 2 molar hydrochloric acid were added at room temperature while stirring vigorously. The clear solution was stirred at from 50° to 60° C. for 2 hours. The reaction solution was then cooled down to from 10° to 20° C. and titrated with 1 molar sodium hydroxide solution to pH 3; the reaction mixture was then diluted with 20 ml of distilled water and concentrated in vacuo until no further dioxane distilled off. On being stirred up with water, a precipitate slowly crystallized and was filtered off with suction and washed with water. After drying at 40° C. under high vacuum, 0.18 g of compound 4 was obtained as a colorless solid.

In this manner, the following compounds of the formula I were synthesized:

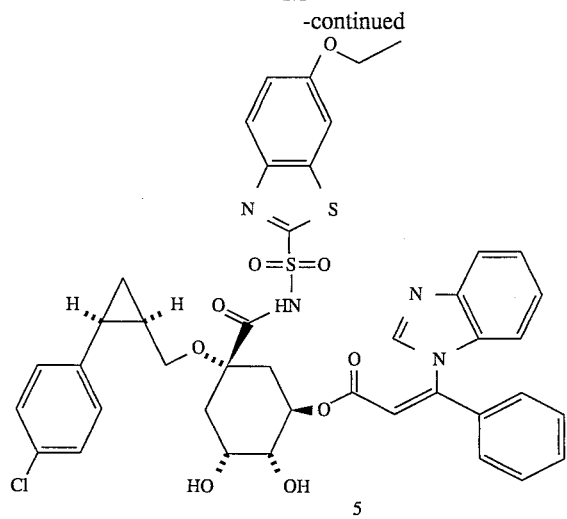
5
MS(FAB):m/z = 843(M + H⁺)
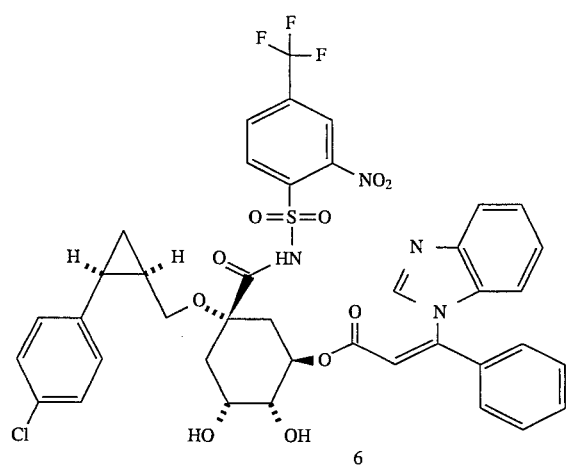
6
MS(FAB):m/z = 855(M + H⁺)
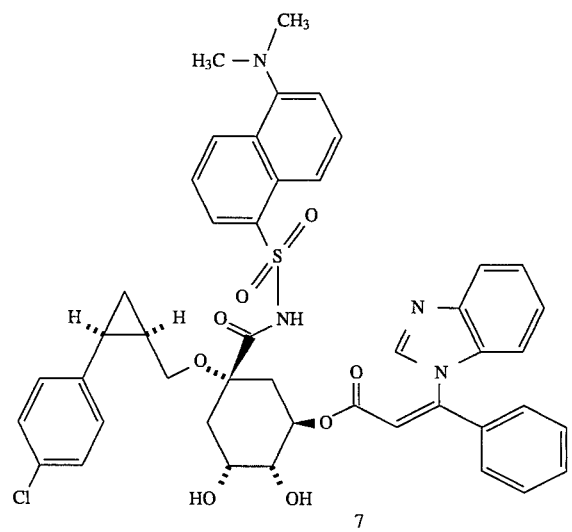
7
MS(FAB):m/z = 835(M + H⁺), 418(M + 2H⁺)

-continued
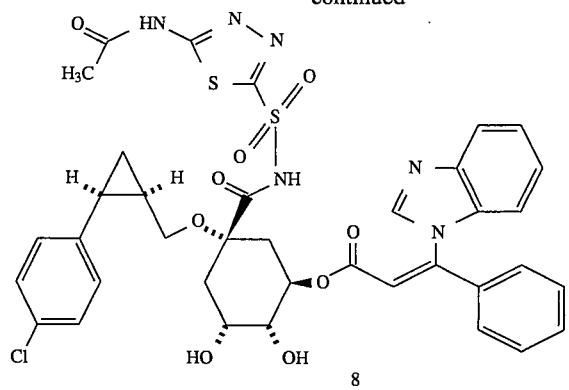
MS(FAB):m/z = 807(M + H+)
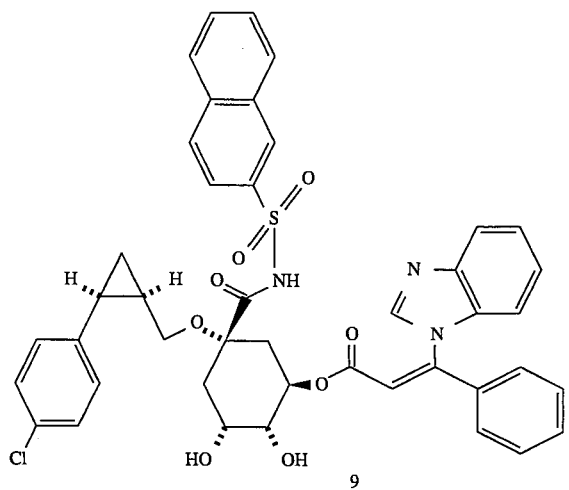
MS(FAB):m/z = 792(M + H+)
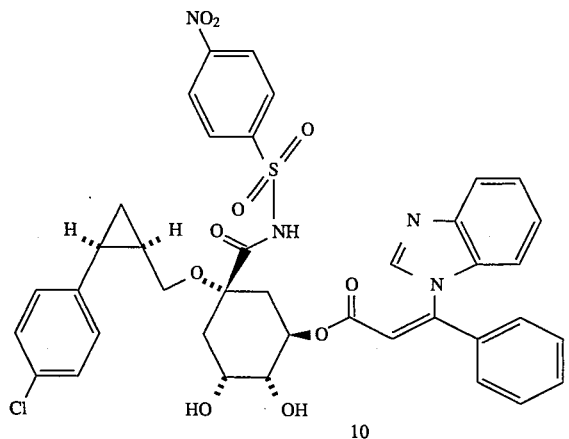
MS(FAB):m/z = 787(M + H+)

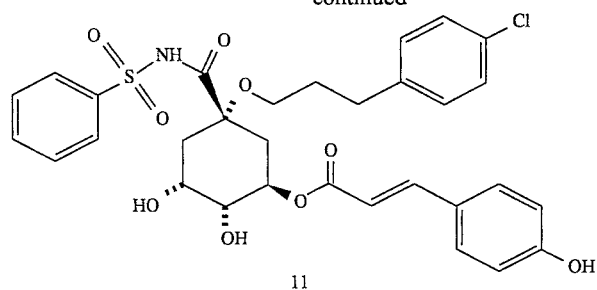
11
MS(FAB):m/z = 630(M + H⁺)
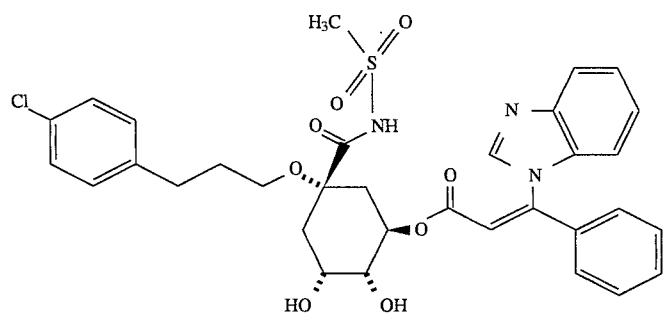
12
MS(FAB):m/z = 668(M + H⁺)
EXAMPLE 2
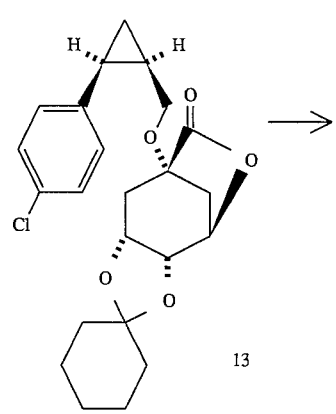
13
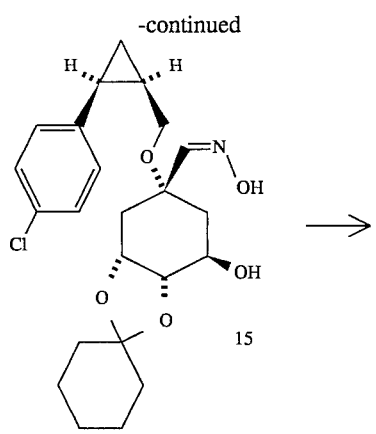
15
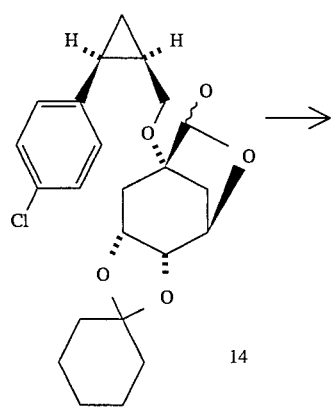
14
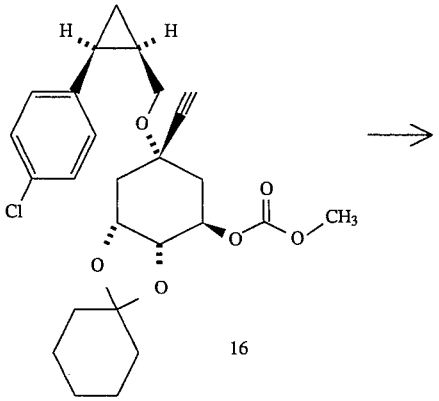
16

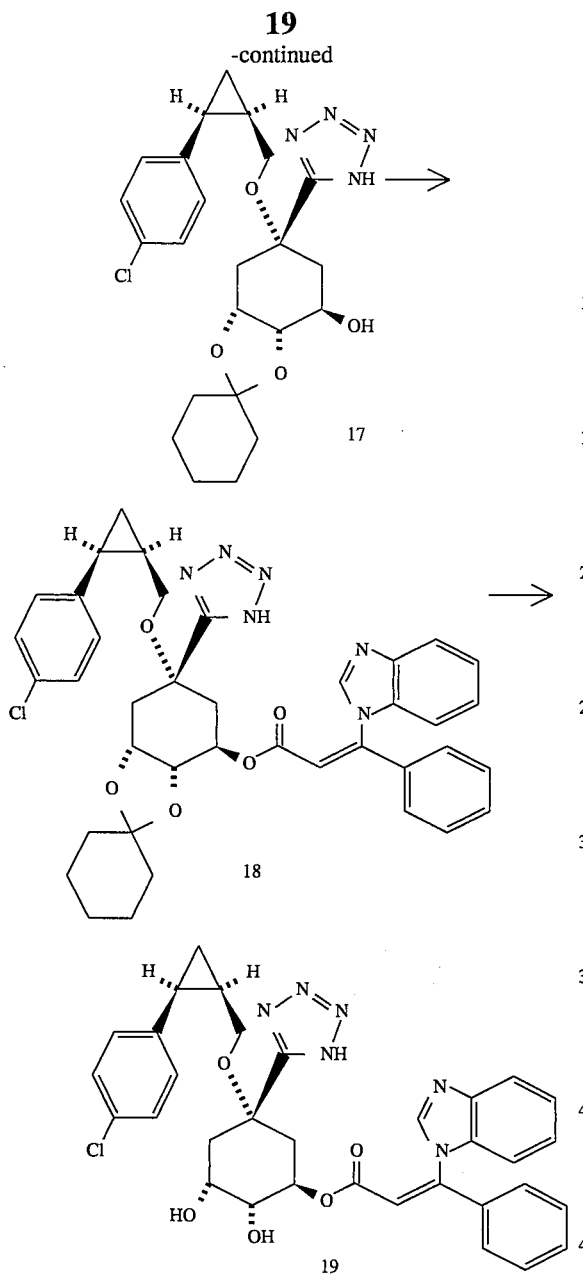

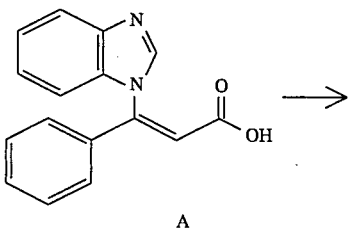

A

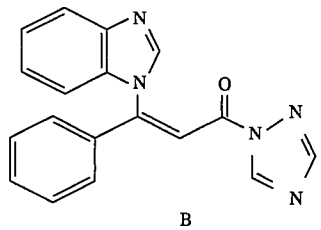

B

Preparation of compound 14 from 13:

5.0 g (0.012 mol) of lactone 13 (preparation cf. EP Application No. 93 114 261.6, reaction scheme method A, structural element 68B) were dissolved in 80 ml of anhydrous toluene, and 10 ml (0.012 mol) of a 1.2 molar solution of diisobutylaluminum hydride in hexane were added dropwise at −78° C. and under an argon atmosphere. After 1 hour at −50° C., hydrolysis was carried out using a saturated solution of ammonium chloride. The mixture was extracted with ethyl acetate and the combined organic phases were washed with a saturated solution of sodium chloride and dried using magnesium sulfate. The organic phase was concentrated in vacuo and the lactol 14 thus obtained was employed in the subsequent step without any further purification.

Preparation of compound 15 from 14:

4.6 g (0.011 mol) of lactol and 0.761 g (0.011 mol) of hydroxylamine hydrochloride were dissolved in 50 ml of methanol. 750 mg (0.014 mol) of potassium hydroxide were added. This solution was stirred at room temperature for 1 hour. 300 ml of methyl tert-butyl ether were then added to the solution, and this was followed by washing with water and with a saturated solution of sodium chloride; after drying with magnesium sulfate, the organic phase was concentrated in vacuo. The residue was purified by chromatography on silica gel (eluent: ethyl acetate/n-heptane 1:2). 3.6 g of oxime 15 were obtained as a colorless oil.

Preparation of compound 16 from 15:

20.0 g (0.046 mol) of oxime 15 were initially introduced in 200 ml of anhydrous dichloromethane, and 23.0 g (0.14 mol) of N,N'-carbonyldiimidazole were added. There followed a powerful evolution of gas. After 14 hours at room temperature, 100 ml of methanol were added to the reaction solution, and the mixture was heated under reflux for a further 4 hours. For the working-up, the solution was brought to dryness by rotary evaporation and the residue was taken up in methyl tert-butyl ether. The organic phase was washed with a mixture of water/0.1M solution of potassium hydrogen sulfate, dried using magnesium sulfate and concentrated in vacuo. The residue was purified by chromatography on silica gel (silica gel particle size: 35 to 70 μm, eluent system: ethyl acetate/n-heptane 1:5, towards the end, the proportion of n-heptane was decreased: 1:3). 12.9 g of nitrile 16 were obtained as a colorless oil.

Preparation of compound 17 from 16:

12.9 g (0.0286 mol) of nitrile 16 were dissolved in 250 ml of anhydrous toluene and heated at 110° C. 5.89 g (0.0286 mol) quantities of trimethyltin azide were added at 24-hour intervals over a period of three days. The reaction solution was then concentrated in vacuo, and 50 ml of 10 molar sodium hydroxide solution and 20 ml of tetrahydrofuran were added to the residue while stirring vigorously. The resulting sodium salt of 17 was filtered off with suction and then suspended in distilled water and this suspension was acidified with 2 molar acetic acid. It was extracted with ethyl acetate and the combined organic phases were dried using magnesium sulfate and concentrated in vacuo. 7.7 g of tetrazole 17 were obtained.

Preparation of starting compound B from A:

274 mg (0.001 mol) of carboxylic acid A (preparation cf. EP Application No. 93 114 261.6, method I) were dissolved, under an argon atmosphere and at room temperature, in 20 ml of anhydrous dimethylformamide, and 180.4 mg (0.0011 mol) of N,N'-carbonyldi-(1,2,4-triazole) were added. The reaction solution was stirred at 60° C. for 1 hour. The resulting solution of compound B was employed in the subsequent step without any further working-up.

Preparation of compound 18 from 17:

3.0 g (0.00652 mol) of compound 17 were dissolved, under an argon atmosphere, in 30 ml of anhydrous dimethylformamide, and 0.70 g (0.023 mol) of sodium hydride (80% dispersion in oil) was added at room temperature. After 1 hour, 157 ml (0.0078 mol) of an 0.5 molar solution of B in dimethylformamide were added dropwise, and the mixture was stirred once again at room temperature for 1 hour. The reaction solution was subsequently added to a saturated solution of ammonium chloride, and this mixture was extracted with ethyl acetate. The combined organic phases were washed with a saturated solution of sodium chloride, dried over magnesium sulfate and concentrated in vacuo. The crude product was purified by chromatography. (Silica gel particle size: 35 to 70 μm, eluent system: ethyl acetate/n-heptane/methanol/glacial acetic acid 30:10:2:1). The ester 18 was obtained as an amorphous solid.

Preparation of compound 19 from 18:

3.8 g (0.0053 mol) of cyclohexylidene compound 18 were taken up in 150 ml of dioxane, and 10 ml (0.02 mol) of 2 molar hydrochloric acid were added while stirring. This solution was heated at 60° C. for 2 hours. The pH of the reaction solution was then adjusted to 3 using 18 ml of 1N molar sodium hydroxide solution and the solvent was removed by rotary evaporation. The residue was taken up in ethyl acetate and the precipitate which developed was filtered off. The filtrate was concentrated in vacuo and the residue was purified by chromatography on silica gel (silica gel particle size: 35 to 70 μm, eluent system: ethyl acetate/methanol/water/glacial acetic acid 4:1:1:0.5). 2.5 g of compound 19 were obtained as a colorless amorphous solid.

In this manner, the following compounds of the formula I were synthesized:

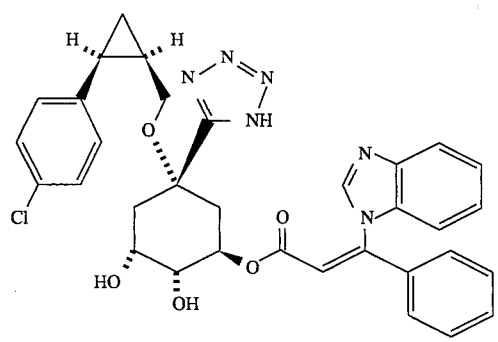

19

MS (FAB): m/z = 627 (M + H⁺)

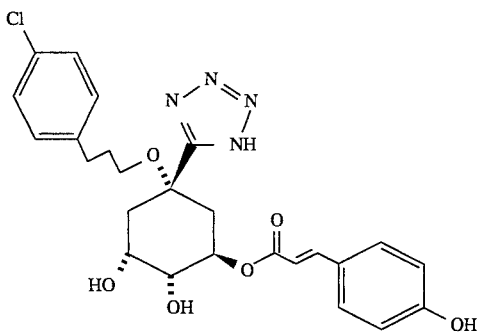

20

MS (FAB): m/z = 515 (M + H⁺)

EXAMPLE 3

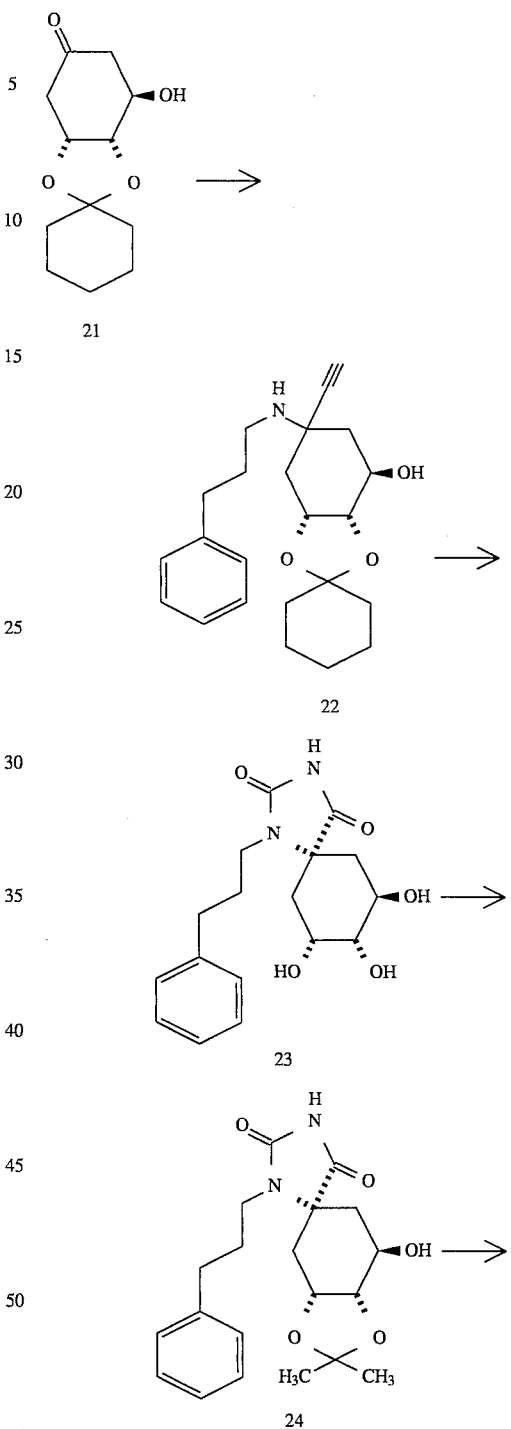

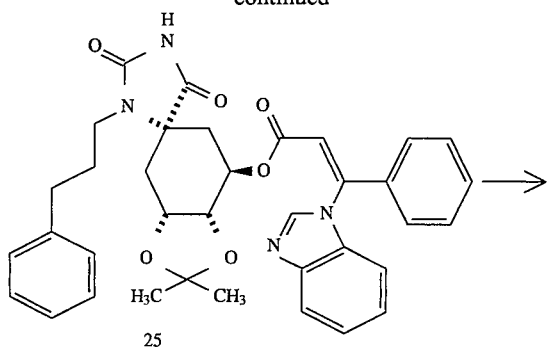

25

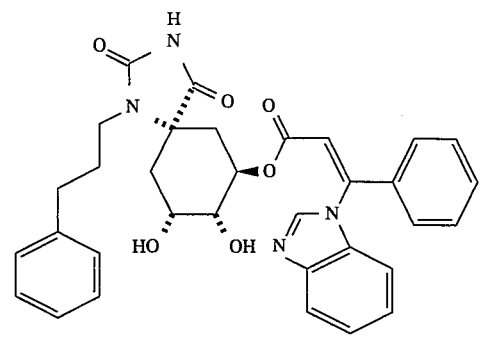

26

Preparation of compound 22 from 21:

2.26 g (0.01 mol) of the ketone 21 which is known from the literature (cf. J. C. Barrier et al., Helv. Chim. Acta 66, 296 (1983)) and 4.29 g (0.025 mol) of 3-phenylpropylamine hydrochloride were initially introduced, under an argon atmosphere, in 5 ml of methanol and 3 ml of distilled water. The mixture was cooled to 0° C. and a solution of 1.63 g (0.025 mol) of potassium cyanide in 4 ml of distilled water was added dropwise. The reaction mixture was stirred at 0° C. for 4 hours and at room temperature for 1 hour and was then added, while stirring, to ice/water; this mixture was extracted three times with ethyl acetate. The combined organic phases were washed three times with distilled water and once with a saturated solution of sodium chloride and then dried using magnesium sulfate and concentrated in vacuo. 5.0 g of crude product 22 were obtained, which product was employed in the subsequent step without any further purification.

Preparation of compound 23 from 22:

3.7 g (0.01 mol) of cyano compound 22 were dissolved in 8 ml of glacial acetic acid, and a solution of 1.62 g (0.02 mol) of potassium cyanate in 4 ml of distilled water was added at room temperature and while stirring. The reaction solution was stirred at room temperature for 75 minutes and then added to a mixture of ice and waters this new mixture was extracted twice with ethyl acetate, and the combined organic phases were washed once with distilled water and once with a saturated solution of sodium chloride. After the organic phase had been dried with magnesium sulfate, it was concentrated in vacuo; the oily residue thus obtained was dissolved in 4 ml of dioxane, and 10 ml of 2 molar hydrochloric acid were added to this solution while stirring. After stirring at 55° C. for one hour, the reaction mixture was poured onto an ice/water mixture and the whole was extracted three times with ethyl acetate. The organic phases were washed three times with water and once with a saturated solution of sodium chloride, dried over magnesium sulfate and concentrated in vacuo. The oily residue was purified by chromatography on silica gel (silica gel particle size: 35 to 70 μm, eluent: ethyl acetate/n-heptane/methanol/glacial acetic acid 20:10:2:1), and 0.36 g of product 23 was obtained.

Preparation of compound 24 from 23:

0.36 g (0.00106 mol) of compound 23 was dissolved in 1.09 ml (0.0106 mol) of dimethoxypropane and 20 ml of anhydrous dichloromethane. 26 mg (10 mol %) of pyridinium para-toluenesulfonate were added. The mixture was heated at 40° C. for 45 minutes. The reaction solution was then added to a saturated solution of sodium hydrogen sulfate and this mixture was extracted with ethyl acetates the combined organic phases were dried using magnesium sulfate. The residue was purified by chromatography on silica gel (silica gel particle size: 35 to 70 μm, eluent system: ethyl acetate/n-heptane 2:1), and 0.24 g of compound 24 was obtained as a colorless solid.

Preparation of compound 25 from 24:

230 mg (0.0006 mol) of hydroxy compound 24 were dissolved in 10 ml of anhydrous dimethylformamide, and 55 mg (0.00184 mol) of sodium hydride (80% dispersion in oil) were added at room temperature and under an argon atmosphere. After 30 minutes at room temperature, 22 ml of a 0.5 molar solution of B in dimethylformamide were added dropwise. After a further 30 minutes at this temperature, a clear solution was obtained; a saturated solution of ammonium chloride was added to this clear solution, whereupon the product 25 precipitated out as an amorphous solid. This solid was filtered off with suction and dried in vacuo. 310 mg of compound 25 were obtained.

Preparation of compound 26 from 25:

290 mg (0.00047 mol) of compound 25 were dissolved in 30 ml of dioxane, and 4 ml (0.008 mol) of 2 molar hydrochloric acid were added, at room temperature and while stirring vigorously, to this solution. After stirring at 50° C. for two hours, the reaction solution was cooled down to from 10° to 20° C. and titrated to pH 3 using 1 molar sodium hydroxide solution. The solution was concentrated in vacuo and the oily residue was taken up in isopropanol; the precipitate of salt was-filtered off and the filtrate was concentrated once again in vacuo. The residue was stirred up with methyl tert-butyl ether and the amorphous precipitate was filtered off with suction. After drying in vacuo, 140 mg of compound 26 (end product of the formula I) were obtained.

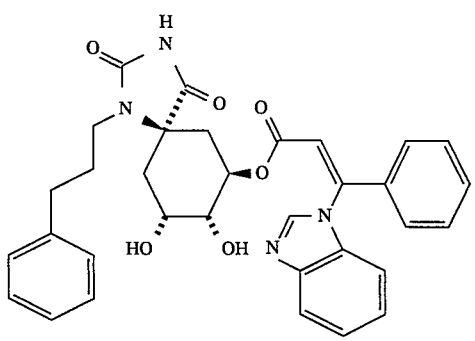

26

MS (FAB): m/z = 581 (M + H$^+$)

EXAMPLE 4

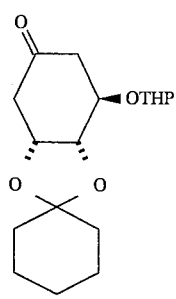

27

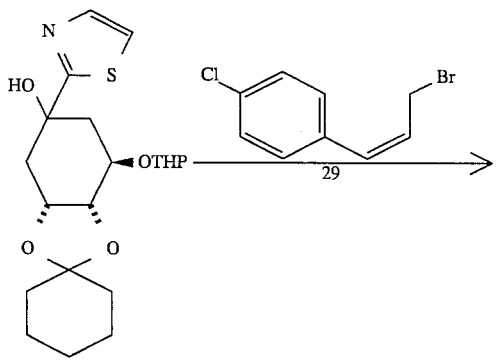

28

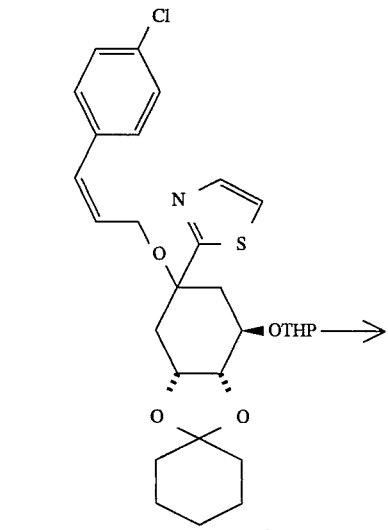

31

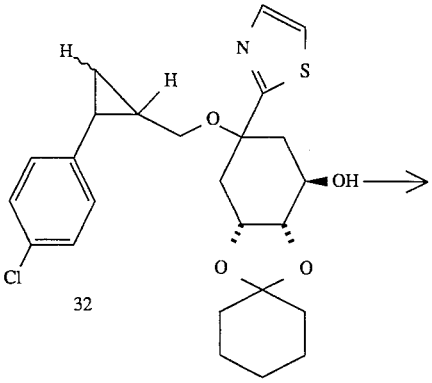

32

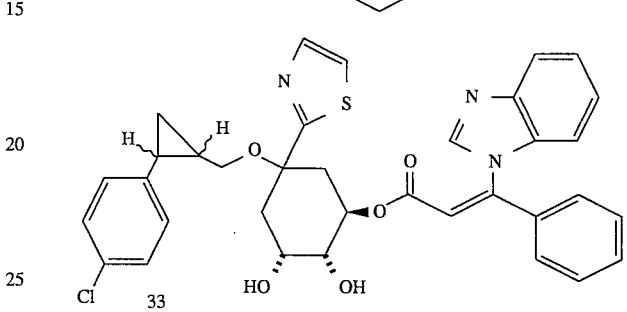

33

Preparation of compound 28 from 27:

6.4 g (14.5 ml, 0.161 mol) of 2-bromothiazole were dissolved, under an argon atmosphere, in 500 ml of anhydrous diethyl ether, and 107.5 ml of n-butyllithium in hexane (1.5 molar solution) were added dropwise at −78° C. The mixture was stirred at −78° C. for 30 minutes and a solution of 25.0 g (0.081 mol) of ketone 27 (cf. EP Application No. 92 114 260.8, formula scheme 4, compound 23B) in 50 ml of anhydrous tetrahydrofuran was then added dropwise. The reaction solution was allowed to heat up to −30° C. within the space of 30 minutes. After that, the reaction solution was added to ammonium chloride solution, and this mixture was extracted with ethyl acetate and the combined organic phases were washed with a saturated solution of sodium chloride and dried using sodium sulfate. The organic phase was concentrated in vacuo and the residue was purified by chromatography on silica gel (eluent: ethyl acetate/heptane 1:2, particle size: 35 to 70 μm). 23.3 g (77%) of compound 28 were obtained as a viscous oil.

Preparation of compound 30 from 28:

15.0 g (0.038 mol) of alcohol 28 were dissolved in 250 ml of anhydrous dimethylformamide, and 1.5 g (0.05 mol) of sodium hydride were added at from 0° to 10° C. The mixture was stirred at 10° C. for 1.5 hours and then cooled down to 0° C., when 13.2 g (0.057 mol) of cis-3-(4-chlorophenyl) propenyl bromide (29), dissolved in 30 ml of anhydrous dimethylformamide, were added dropwise. The reaction solution was allowed to warm to room temperature and was stirred at this temperature for 2 hours. The reaction solution was subsequently added to a saturated solution of ammonium chloride and this mixture was extracted with ethyl acetates the combined organic phases were washed with a saturated solution of sodium chloride. After having been dried using sodium sulfate, the organic phase was concentrated in vacuo and the residue was purified by chromatography on silica gel (eluent: ethyl acetate/n-heptane 1:2, particle size: 35 to 70 μm). 19.0 g of thiazole 30 were obtained as a viscous oil.

Preparation of compound 31 from 30:

27

56.6 ml of a 1.1 molar solution of diethylzinc in toluene were added dropwise, at 0° C. and under an argon atmosphere, to 250 ml of anhydrous dichloroethane, and 9.0 ml (0.125 mol) of chloroiodomethane were then added at 0° C. The reaction solution was stirred at the same temperature for 30 minutes and, after that, 17.0 g (0.031 mol) of olefin 30, dissolved in 30 ml of anhydrous dichloroethane, were added dropwise. The mixture was allowed to warm slowly to room temperature. After 2 hours, the reaction solution was added to a saturated solution of ammonium chloride and this mixture was extracted with ethyl acetates the combined organic phases were washed with a saturated solution of sodium chloride. After the organic phase had been dried using sodium sulfate, it was concentrated in vacuo and the residue was stirred thoroughly with methyl tert-butyl ether. The precipitate was filtered off (methylation of the nitrogen in the thiazole ring took place as a side reaction) and the filtrate was concentrated once again. 4.2 g (24%) of compound 31 were obtained as a viscous oil.

Preparation of compound 32 from 31:

4.2 g (0.008 mol) of 31 were dissolved in 100 ml of methanol and 150 ml of dichloromethane, and 0.7 g (0.003 mol) of pyridinium p-toluenesulfonate was added at room temperature. The clear solution was allowed to stand at room temperature for 14 hours and 20 ml of a 1N solution of sodium hydrogen carbonate were then added to it; this mixture was concentrated until only the aqueous phase remained. This phase was extracted with ethyl acetate and the combined organic phases were washed with a saturated solution of sodium chloride, dried using sodium sulfate and concentrated in vacuo. The residue was purified by chromatography on silica gel (eluent: ethyl acetate/n-heptane 1:1, particle size: 35 to 70 μm). 1.82 g (51%) of compound 32 were obtained as a colorless oil.

Preparation of compound 33 from 32:

In analogy with the preparation of compound 19 from compound 17, as described in Example 2, compound 33 of the formula I was obtained, as an amorphous solid, from 32 in 2 stages. MS (FAB): m/z=542 (M+H⁺)

We claim:

1. A cyclohexanol ester of the formula I:

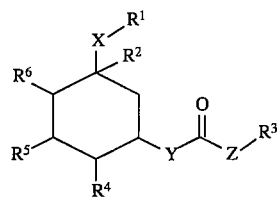

in which the radicals have the following meaning:

$R^1$ is $CONHCOR^{15}$, $CSNHR^{15}$, $CONHSO_2R^{14}$, $CSNHSO_2R^{14}$ or $CH_2NHSO_2R^{14}$, or $R^1$ is a radical selected from the following formulae:

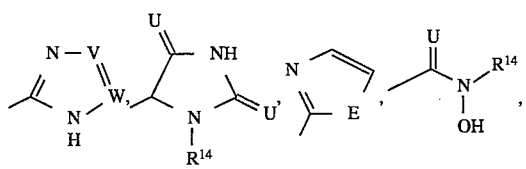

28

-continued

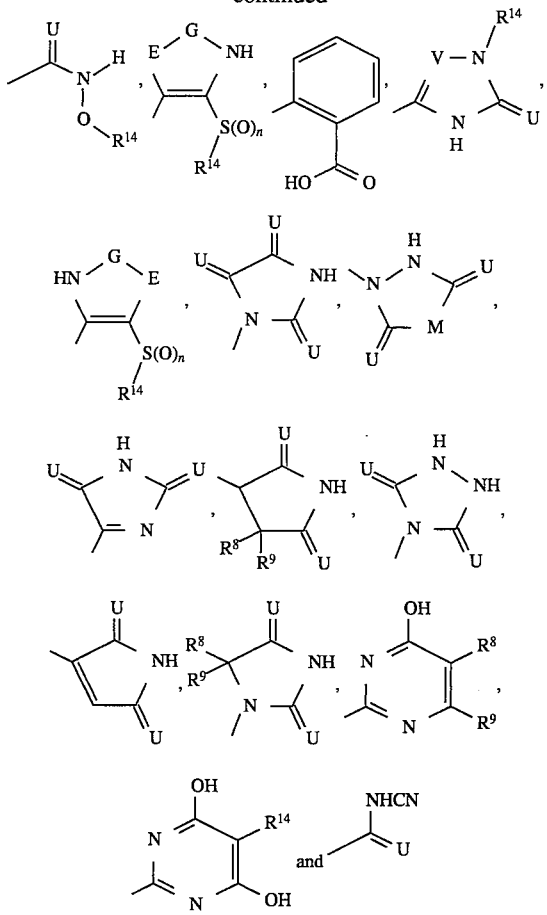

in which V is N or CH, W is N or CH, U is O or S, E is $NR^{14}$, or NH, G is —N=, or

M is $NR^{14}$, NH, $CH_2$ or $CR^8R^9$, and aromatic rings may be substituted at least once by F, Cl, Br, I, OH, $O-C_1-C_4$-alkyl, $C_1-C_4$-alkyl, $CF_3$, $NO_2$ or CN, or $R^1$ forms, together with $R^2$, the ring

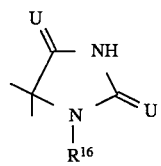

$R^2$ is $C_1-C_{10}$-alkyl$(R^{11})$n, $O-C_1-C_{10}$-alkyl$(R^{11})_n$, $C_2-C_{10}$-alkenyl$(R^{11})$n, $O-C_3-C_{10}$-alkenyl$(R^{11})$, $C_2-C_{10}$-alkynyl$(R^{11})$n, $O-C_3-C_{10}$-alkynyl$(R^{11})$n, $S-C_1-C_{10}$-alkyl$(R^{11})$n, $S-C_3-C_{10}$-alkenyl$(R^{11})$n, $S-C_3-C_{10}$-alkynyl$(R^{11})$n, $NH-C_1-C_{10}$-alkyl$(R^{11})$n, $NH-C_3-C_{10}$-alkenyl$(R^{11})$n or $NH-C_3-C_{10}$-alkynyl$(R^{11})$n, where $R^{11}$ is optionally substituted by $R^{12}$;

$R^{11}$ and $R^{13}$ are alkyl having from 1 to 10 carbon atoms, cycloalkyl having from 3 to 8 ring carbon atoms, phenyl, naphthyl, phenanthryl pyridyl, thienyl, furyl, pyrimidyl, indolyl, imidazolyl, coumarinyl, phthaliminyl, quinolyl, piperazinyl, -tetrazolyl, triazolyl, oxazolyl or their thieno-fused, pyridino-fused, pyrimidino-fused or benzo-fused derivatives, where the aromatic radical or heteroaromatic radical may be substituted at least once, identically or differently, by F, Cl, Br, I, OH, —$NO_2$, CN, $C_1$–$C_4$-alkoxy, $C_1$–$C_4$-alkyl, $NR^8R^9$, phenyl, benzyl, thienyl, furyl, imidazolyl, pyridyl, O-phenyl or O-benzyl, and $R^{11}$ and $R^{13}$ are identical or different; $R^3$ is a benzo-fused derivative of imidazolyl;

$R^4$, $R^5$ and $R^6$ are H, OH, an OH group protected by customary alcohol protective groups, F, Cl or Br, or have the meanings given for $R^2$, where $R^4$, $R^5$ and $R^6$ are identical or different;

$R^8$ and $R^9$ are H, $C_1$–$C_4$-alkyl, $C_1$–$C_4$-alkanoyl or phenyl which is optionally substituted by F, Cl, Br, I, OH, O—$C_1$–$C_4$-alkyl, $CF_3$, —$NO_2$ or CN, where $R^8$ and $R^9$ are identical or different, or $R^8$ and $R^9$ form, together with the nitrogen atom, a 4- to 10-membered, saturated heterocyclic ring in which a $CH_2$ group may be optionally replaced by O, S or $NR^{10}$ $R^{10}$ is H, $C_1$–$C_4$-alkyl, phenyl or benzyl;

$R^{12}$ is phenyl, naphthyl, phenanthryl, pyridyl, thienyl, furyl, thiazolyl, pyrimidyl, indolyl, imidazolyl, coumarinyl, phthaliminyl, quinolyl, piperazinyl, tetrazolyl, triazolyl, oxazolyl or their thieno-fused or benzo-fused derivatives, where the aromatic radical or heteroaromatic radical may be substituted at least once, identically or differently, by F, Cl, Br, I, OH, $CF_3$, —$NO_2$, CN, $C_1$–$C_4$-alkoxy, $C_1$–$C_4$-alkyl, $NR^8R^9$, phenyl, benzyl, thienyl, furyl, imidazolyl, pyridyl, O-phenyl or O-benzyl;

$R^{14}$ is hydrogen, $C_1$–$C_{10}$-alkyl, phenyl, naphthyl, phenanthryl, pyridyl, thienyl, furyl, thiazolyl, pyrimidyl, indolyl, imidazolyl, coumarinyl, phthaliminyl, quinolyl, piperazinyl, tetrazolyl, triazolyl, oxazolyl or their thieno-fused or benzo-fused derivatives, where the aromatic radical or hetero-aromatic radical may be substituted at least once, identically or differently, by F, Cl, Br, I, OH, $CF_3$, —$NO_2$, CN, $C_1$–$C_4$-alkoxy, $C_1$–$C_4$-alkyl, $NR^8R^9$, phenyl, benzyl, thienyl, furyl, imidazolyl, pyridyl, O-phenyl or O-benzyl, or $R^{14}$ is a radical of the formula

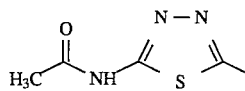

$R^{15}$ is $C_3$–$C_{10}$-alkenoyl, $C_3$–$C_{10}$-alkenoyl($R^{12}$), $C_1$–$C_{10}$-alkanoyl($R^{12}$), phenyl, naphthyl, phenanthryl, pyridyl, thienyl, furyl, thiazolyl, pyrimidyl, indolyl, imidazolyl, coumarinyl, phthaliminyl, quinolyl, piperazinyl, tetrazolyl, triazolyl, oxazolyl or their thieno-fused or benzo-fused derivatives, where the aromatic radical or heteroaromatic radical may be substituted at least once, identically or differently, by F, Cl, Br, I, OH, $CF_3$, —$NO_2$, CN, $C_1$–$C_4$-alkoxy, $C_1$–$C_4$-alkyl, $NR^8R^9$, phenyl, benzyl, thienyl, furyl, imidazolyl, pyridyl, O-phenyl or O-benzyl;

$R^{16}$ is $C_1$–$C_{10}$-alkyl($R^{11}$)n, $C_3$–$C_{10}$ alkenyl($R^{11}$)n or $C_3$–$C_{10}$-alkynyl ($R^{11}$)n, where $R^{11}$ is optionally substituted by $R^{12}$, X is $(CH_2)_m$, —CH=CH—, —C≡C—, —$CH_2$—O—$CH_2$—, —$CH_2$—S—$CH_2$— or

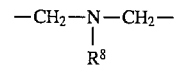

Y is $(CH_2)_m$, O, S or $NR^8$,

Z is $(CH_2)_m$, [S, O, S—$C_1$–$C_{10}$-alkyl, O—$C_1$–$C_{10}$-alkyl,] CH=CH, CH=CF, CH=CCl, CH=CBr, $CH_2$—CO, $CH_2$—CHF, $CH_2$—CHCl, $CH_2$—CHBr, $CH_2$—CHI, C=C, CH=C($C_1$–$C_4$-alkyl), CH=C(CN), CH=C($NR^8R^9$), CH=C($C_1$–$C_4$-alkanoyl), or CH=C($R^{13}$) and, if Y is oxygen,

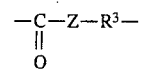

may together be an amino acid residue, selected from the group consisting of Ala, Arg, Asn, Asp, Cys, Gln, Glu, Gly, His, Ile, Leu, Lys, Phe, Pro, Ser, Thr, Trp, Tyr and their derivatives protected by customary protective groups, n is zero, 1 or 2, m is zero, 1, 2, 3 or 4, and also a physiologically tolerated salt of a compound of the formula I.

2. A cyclohexanol ester and its physiologically tolerated salt as claimed in claim 1, wherein the radicals in formula I have the following meanings:

$R^1$ is $CONHCOR^{15}$, $CSNHR^{15}$, $CONHSO_2R^{14}$, $CSNHSO_2R^4$ or $CH_2NHSO_2R^4$, or is a radical of the following formulae:

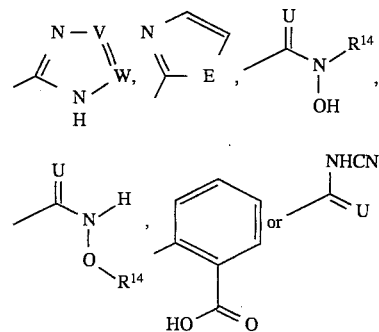

in which E is NH, $R^{14}$ is H, U is O or S, V is N or CH, W is N or CH, and aromatic rings may be substituted at least once by F, Cl, Br, I, OH, O—$C_1$–$C_4$-alkyl, $C_1$–$C_4$-alkyl, $CF_3$, $NO_2$ or CN, or $R^1$ forms, together with $R^2$, the ring

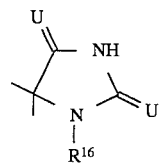

wherein $R^2$ is selected from O—$C_1$–$C_{10}$-alkyl($R^{11}$)$_n$, wherein n is 0, 1, or 2 and where the alkyl moiety is unbranched, branched or cyclic, and $R^{11}$ may be substituted by $R^{12}$, and, when n is 2, the two radicals $R^{11}$ are identical or different; O—$C_3$–$C_{10}$-alkenyl($R^{11}$)$_n$, wherein n is 0, 1, or 2 and where the alkenyl moiety is unbranched, branched or cyclic, and is unsaturated at least once, and $R^{11}$ may be substituted by $R^2$, and, when n is 2, the two radicals $R^{11}$ are identical or different; and $O-C_3-C_{10}$-alkynyl$(R^{11})_n$, wherein, n is 0, 1, or 2 and where the alkynyl moiety is unbranched, branched or cyclic, and is unsaturated at least once, and $R^{11}$ may be substituted by $R^{12}$, X is $(CH_2)_m$ wherein m is 0, 1, 2, 3, or 4, CH=CH, C≡C, $CH_2OCH_2$ or $CH_2SCH_2$, Y is $(CH_2)_m$ wherein m is 0, 1, 2, 3, or 4, O, S, or $NR^8$, Z is $(CH_2)_m$ wherein m is 0, 1, 2, 3, or 4, CH=CH, CH=CF, CH=CCl, CH=CBr, $CH_2$—CO, $CH_2$—CHF, $CH_2$—CHCl, $CH_2$—CHBr, $CH_2$—CHI, C≡C, CH=C($C_1$-$C_4$-alkyl), CH=C(CN), or CH=C($R^{13}$), $R^3$ to $R^{15}$ have the meanings given in claim 1.

3. A cyclohexanol ester and its physiologically tolerated salt as claimed in claim 1, wherein the radicals in formula I have the following meanings:

$R^1$ is $CONHCOR^{15}$, $CSNHR^{15}$, $CONHSO_2R^{14}$, $CSNHSO_2R^{14}$ or a radical of the formulae:

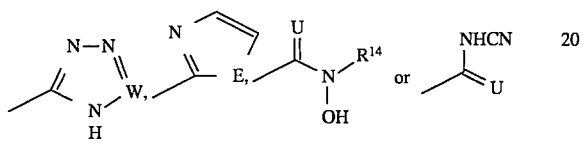

in which E is NH, $R^{14}$ is H, U is O or S, V is N or CH, W is N or CH, and aromatic rings may be substituted at least once by F, Cl, Br, I, OH, O—$C_1$-$C_4$-alkyl, $C_1$-$C_4$-alkyl, $CF_3$, $NO_2$ or CN, or $R^1$ forms, together with $R^2$, the ring

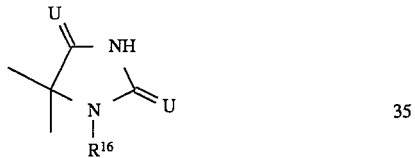

wherein $R^2$ is selected from O—$C_1$-$C_{10}$-alkyl$(R^{11})_n$, wherein n is 0, 1, or 2 and where the alkyl moiety is unbranched, branched or cyclic, and $R^{11}$ may be substituted by $R^{12}$, and, when n is 2, the two radicals $R^{11}$ are identical or different;

O—$C_3$-$C_{10}$-alkenyl$(R^{11})_n$, where n is 0, 1, or 2 and where the alkenyl moiety is unbranched, branched or cyclic, and is unsaturated at least once, and $R^{11}$ may be substituted by $R^{12}$, and, when n is 2, the two radicals $R^{11}$ are identical or different; and O—$C_3$-$C_{10}$-alkynyl$(R^{11})_n$, wherein n is 0, 1, or 2 and where the alkynyl moiety is unbranched, branched or cyclic, and is unsaturated at least once, and $R^{11}$ may be substituted by $R^{12}$, X is $(CH_2)_m$ wherein m is 0, 1, 2, 3, or 4, CH=CH, C≡C, $CH_2OCH_2$ or $CH_2SCH_2$, Y is $(CH_2)_m$ wherein m is 0, 1, 2, 3, or 4, O, S, or $NR^8$, Z is $(CH_2)_m$ wherein m is 0, 1, 2, 3, or 4, CH=CH, CH=CF, CH=CCl, CH=CBr, $CH_2$—CO, $CH_2$—CHF, $CH_2$—CHCl, $CH_2$—CHBr, $CH_2$—CHI, C≡C, CH=C($C_1$-$C_4$-alkyl) which is unbranched or branched, CH=C(CN), or CH=C($R^{13}$), $R^{16}$ is $C_1$-$C_{10}$-alkyl$(R^{11})_n$, $C_3$-$C_{10}$-alkenyl$(R^{11})_n$ or $C_3$-$C_{10}$-alkynyl $(R^{11})_n$, with n in each case being zero or 1, $R^3$ to $R^{15}$ have the meanings given in claim 1.

4. A cyclohexanol ester and its physiologically tolerated salt as claimed in claim 1, wherein the radicals in formula I have the following meanings:

$R^1$ is $CONHSO_2R^{14}$ or a radical of the following formula:

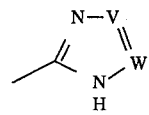

in which, V is N and W is N, or $R^1$ forms, together with $R_2$, the ring

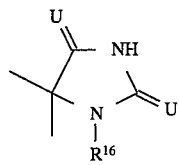

in which U is oxygen, $R^2$ is O—$C_1$-$C_6$-alkyl$(R^{11})_n$, wherein n is 1 and where the alkyl moiety is unbranched, branched or cyclic, or O—$C_1$-$C_6$-alkenyl$(R^{11})_n$, wherein n is 1 and where the alkyl moiety is unbranched, branched or cyclic, $R^{11}$ and $R^{13}$ are phenyl, phenyl substituted by OH or chlorine, imidazolyl or benzo-fused or pyridino-fused imidazolyl, where $R^{11}$ and $R^{13}$ are identical or different, $R^3$ is a benzo-fused derivative or imidazolyl, $R^4$, $R^5$ and $R^6$ are H or OH, where $R^4$, $R^5$ and $R^6$ are identical or different, $R^8$ and $R^9$ are $C_1$-$C_4$-alkyl, $R^{14}$ is $C_1$-$C_4$-alkyl, phenyl, naphthyl, thiazolyl or its benzo-fused derivatives, where the aromatic radical or heteroaromatic radical may be monosubstituted or disubstituted by chlorine, $CF_3$, $NO_2$, $C_1$-$C_4$-alkoxy or $NR^8R^9$, or $R^{14}$ is a radical of the formula

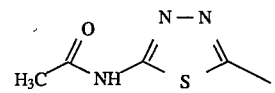

$R^{16}$ is $C_1$-$C_4$-alkyl$(R^{11})_n$, with n being 1.

5. A method for treating diseases which are associated with an elevated activity of the glucose-6-phosphatase system comprising administering an effective amount of a compound as claimed in claim 1 to a patient in recognized need of such treatment.

6. A method for treating diseases which are associated with an elevated production of glucose in the liver comprising administering an effective amount of a compound as claimed in claim 1 to a patient in recognized need of such treatment.

7. A method for treating type II diabetes comprising administering an effective amount of a compound as claimed in claim 1 to a patient in recognized need of such treatment.

8. A pharmaceutical composition comprising a compound as claimed in claim 1 and a pharmaceutically acceptable carrier.

9. A pharmaceutical composition comprising a compound as claimed in claim 2 and a pharmaceutically acceptable carrier.

10. A pharmaceutical composition comprising a compound as claimed in claim 3 and a pharmaceutically acceptable carrier.

11. A pharmaceutical composition comprising a compound as claimed in claim 4 and a pharmaceutically acceptable carrier.

* * * * *

UNITED STATES PATENT AND TRADEMARK OFFICE
CERTIFICATE OF CORRECTION

PATENT NO. : 5,567,725
DATED : October 22, 1996
INVENTOR(S) : Horst HEMMERLE et al.

It is certified that error appears in the above-indentified patent and that said Letters Patent is hereby corrected as shown below:

Claim 1, column 28, line 55, "O—$C_1$–$C_{10}$-alkyl$(R^{11})_n$" should read --O—$C_1$–$C_{10}$-alkyl$(R^{11})$n--.

Claim 1, column 28, line 56, "O—$C_3$–$C_{10}$-alkenyl$(R^{11})$," should read --O—$C_3$–$C_{10}$-alkenyl$(R^{11})$n--.

Claim 1, column 30, line 6, delete, "[S, O, S—$C_1$–$C_{10}$-alkyl, O—$C_1$–$C_{10}$-alkyl,]"

Claim 1, column 30, line 19, "lie" should read --Ile--.

Claim 2, column 30, line 29, "$CSNHSO_2R^4$" should read --$CSNHSO_2R^{14}$-- and "$CH_2NHSO_2R^4$" should read --$CH_2NHSO_2R^{14}$--.

Claim 2, column 30, line 67, "$R^2$" should read --$R^{12}$--.

Claim 2, column 31, line 11, "CH=C($C_1$1–$C_4$-" should read --CH=C($C_1$–$C_4$---.

UNITED STATES PATENT AND TRADEMARK OFFICE
CERTIFICATE OF CORRECTION

PATENT NO. : 5,567,725
DATED : October 22, 1996
INVENTOR(S) : Horst HEMMERLE et al.

It is certified that error appears in the above-indentified patent and that said Letters Patent is hereby corrected as shown below:

Claim 3, column 31, line 20 (1st formula),

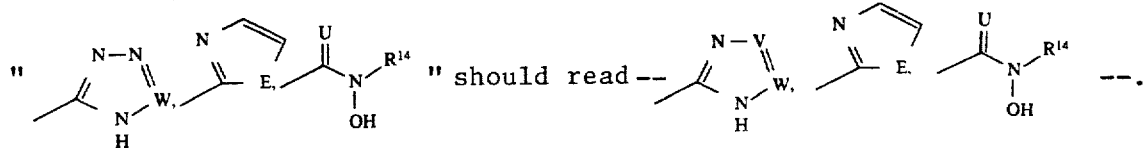

Claim 3, column 31, line 43, "where" should read --wherein--.

Claim 8, column 32, line 54;

Claim 9, column 32, line 57;

Claim 10, column 32, line 60; and

Claim 11, column 32, line 63, after "comprising", insert --an effective amount of--.

Signed and Sealed this

Nineteenth Day of August, 1997

Attest:

BRUCE LEHMAN

*Attesting Officer*     *Commissioner of Patents and Trademarks*